(12) United States Patent
Nakano et al.

(10) Patent No.: US 6,914,075 B2
(45) Date of Patent: Jul. 5, 2005

(54) CYSTINE DERIVATIVE AND AGENT FOR SUPPRESSING ACTIVATION OF INFLAMMATORY FACTORS

(75) Inventors: Takashi Nakano, Kawasaki (JP); Manabu Kitazawa, Kawasaki (JP); Keiji Iwasaki, Kawasaki (JP); Kazutami Sakamoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/632,959

(22) Filed: Aug. 4, 2003

(65) Prior Publication Data

US 2004/0059110 A1 Mar. 25, 2004

Related U.S. Application Data

(63) Continuation of application No. PCT/JP02/00222, filed on Jan. 16, 2002.

(30) Foreign Application Priority Data

Feb. 2, 2001 (JP) .......................................... 2001-027367

(51) Int. Cl.$^7$ .................... A61K 31/225; C07C 229/00; A61P 29/00
(52) U.S. Cl. ........................ 514/547; 560/155; 560/160
(58) Field of Search ................................ 560/155, 160; 514/547

(56) References Cited

FOREIGN PATENT DOCUMENTS

| EP | 1 120 407 A1 | 8/2001 |
| WO | WO 00/27378 | * 5/2000 |

OTHER PUBLICATIONS

Baerlocher et al, CAS:136:385699.*

U.S. Appl. No. 10/632,959, filed Aug. 4, 2003, Nakano et al.

U.S. Appl. No. 10/469,985, filed Sep. 15, 2003, Iwasaki et al.

* cited by examiner

*Primary Examiner*—Rita Desai
*Assistant Examiner*—Robert Shiao
(74) *Attorney, Agent, or Firm*—Oblon, Spivak, McClelland, Maier & Neustadt, P.C.

(57) ABSTRACT

The present invention provides cystine derivatives, which may be in a free form, a salt form, a solvate form. The cystine derivatives of the present invention may be used to suppress activation of inflammatory factors. Accordingly, the present invention provides: compositions containing the cystine derivatives; a method for suppressing the activation of inflammatory factors by administering the composition; a method for preventing, ameliorating and/or therapeutically treating diseases, skin injuries or disorders involved in the activation of inflammatory factors by administering the composition; a method for preventing, delaying, ameliorating and/or therapeutically treating skin change via aging or aesthetically unfavorable skin change as induced or promoted by inflammatory factors by administering the composition; and pharmaceutical agents containing the cystine derivatives.

20 Claims, No Drawings

US 6,914,075 B2

CYSTINE DERIVATIVE AND AGENT FOR SUPPRESSING ACTIVATION OF INFLAMMATORY FACTORS

CROSS-REFERENCE TO RELATED APPLICATIONS

The present application is a continuation application of PCT International Application No. PCT/JP02/00222, filed on Jan. 16, 2002, which is hereby incorporated by reference in its entirety. In addition, the present application claims priority to Japanese Patent Application No. 2001-27367, filed on Feb. 2, 2001, which is hereby incorporated by reference in its entirety.

BACKGROUND OF THE INVENTION

1. Field of the Invention

The present invention relates to a novel cystine derivative and a method for producing the same, a composition for suppressing the activation of inflammatory factors, which is useful for the prevention, amelioration and/or therapeutic treatment of diseases related to inflammatory factors, such as diseases involved in the activation of inflammatory factors and inflammatory diseases (disorders) or dermal damages based on the activation and which contains the novel derivative as an effective ingredient. The present invention also relates to a method for suppressing the activation of inflammatory factor using a composition containing the novel cystine derivatives for suppressing the activation of inflammatory factors.

In more specific aspects of the composition for suppressing the activation of inflammatory factors, the invention relates to pharmaceutical agents (pharmaceutical products), particularly external skin application agents, eye drops, nutrition agents, transfusion or the like, cosmetics (including additives for cosmetics), foods or drinks (health foods or drinks or the like), and the like, which contain the cystine derivative with the action to suppress the activation of inflammatory factors as the effective ingredient.

Additionally, the invention relates to a method for suppressing the activation of inflammatory factors, a use of the specific active ingredient thereof (the effective ingredient described above) for the composition for suppressing the activation of inflammatory factors, and the like.

2. Discussion of the Background

In recent years, intensive investigations have been focused on examining the pathogenesis of various diseases and dermal damages caused by the activation of inflammatory factors induced by ultraviolet ray and by oxidative stress with active oxygen, free radicals, and various psychological stress. It has been determined that iron released from proteins (transferrin, lactoferrin, ferritin and the like) in biological organisms via oxidative stress functions as a catalyst to promote the generation of free radical (the Fenton reaction) (see for example Journal of Investigative Dermatology, Vol. 97, 1991, pp. 1044–1047). Additionally, it has also been determined that inflammatory cytokines such as IL-1α and TNF-α and extracellular matrix decomposition enzymes, such as collagenase, are deeply involved causatively in aging, oncogenesis, pigmentation, inflammation and the like (see for example "Oxidative Stress in Dermatology", Marcel Dekker, Inc., pp. 187–205, 1993).

The expression of genes encoding the aforementioned proteins is mainly regulated at the transcription level of the genes. With respect to inflammatory proteins (such as inflammatory cytokines and extracellular matrix decomposition enzymes) transcription regulators or regulatory factors (such as NF-κB and AP-1) regulate the expression thereof (see for example "Active Oxygen and Signal Transmission", Kodansha Scientific, pp. 37–46, 1996). Therefore; it is hypothesized that oxidative stress may be reduced and/or diseases and damages involved in the activation of inflammatory factors may be prevented, when the generation of free radical can be suppressed via the capture of released iron ion involved in the promotion of the generation of free radical and/or when the expression of inflammatory proteins and the activation of transcription regulators involved therein can be suppressed.

In the past, it has been discovered that amino acid derivatives for example N-(2-hydroxybenzyl)-L-serine and N-(2-hydroxybenzyl)-glycine (see for example Biochimica et Biophysica Acta, Vol. 1473, 1999, pp. 400–408; and U.S. Pat. No. 5,594,012) and chelators such as desferrioxamine (see for example Free Radical Research, Vol. 20, 1994, pp. 83–101) capture iron ion to reduce oxidative stress. Further, it has been discovered that sulfur-containing anti-oxidants, such as N-acetyl-L-cysteine, N,N'-diacetyl-L-cystine dimethyl ester and pyrrolidine dithiocarbamate, suppress the activation of NF-κB (see for example "Active Oxygen and Signal Transmission", Kodansha Scientific, pp. 37–46, 1996; and WO 00/21925). It has also been reported that N-acetyl-L-cysteine and N,N'-diacetyl-L-cystine dimethyl ester also suppress the activation of AP-1 (see for example FEBS Letters, Vol. 384, pp. 92–96, 1996; and WO 00/21925).

However, disadvantageously, the aforementioned compounds have proven to have insufficient in vivo effes and desferrioxamine, pyrrolidine dithiocarbamate, and the like, have strong toxicity on cells. Other than chelators and sulfur-containing anti-oxidants, for example, reports demonstrate that retinoic acid activates AP-1 and suppresses the expression of extracellular matrix decomposition enzymes (see for example Nature, Vol. 379, pp. 335–339, 1996) and that steroidal anti-inflammatory agents or non-steroidal anti-inflammatory agents suppress the activation of NF-κB (see for example Bio Assays, Vol. 18, pp. 371–378, 1996). However, retinoic acid and steroidal anti-inflammatory agents have adverse effects in vivo such as dermal detachment and steroidal dermatitis, respectively. Therefore, the use thereof is limited. Non-steroidal anti-inflammatory agents still remain to be improved of their local adverse effects and have insufficient effects on the suppression of the activation of inflammatory factors, although non-steroidal anti-inflammatory agents have no systemic adverse effects caused by steroidal anti-inflammatory agents.

Skin change via aging or aesthetically unfavorable skin changes are disorders, dermal damages, and/or diseases caused by the activation of inflammatory factors. A method for preventing or delaying such a change has been reported. This method entails coating a combination of natural extracts with an action to ameliorate rough skin and the like, such as astaxanthin or ingredients contained therein, with cystine derivatives on skin (see for example Japanese Patent Kokai Publication JP-A-9-143063). This combination can enhance the recovery of tension or luster of skin or can ameliorate the darkness of skin, but the effect thereof is not sufficient. Additionally, the effect thereof on the most prominent skin wrinkle or looseness among senile skin findings has not been demonstrated.

The induction or promotion of skin wrinkles or looseness is a representative example of the skin change via aging or aesthetically unfavorable skin change caused by the activation of inflammatory factors, which are induced via oxidative or psychological stresses. The cause of these stresses includes sunlight, ultraviolet ray in sunlight or ultraviolet ray in other light sources (see for example "New Cosmetology", Nanzando, pp. 38–46, 1993). A method for preventing or delaying these phenomena has been reported and entails coating an anti-oxidant, such as tocopherol, ascorbic acid or N-acetyl-L-cystine on skin (see for example Photodermatol. Photoimmunol. Photomed., Vol. 7, pp. 56–62, 1990; and Japanese Patent Kohyo Publication JP-A-6-510542). In addition to anti-oxidants, some anti-inflammation agents or ultraviolet absorbents have been demonstrated to have effects on the prevention or delay of induction or promotion of skin wrinkles or looseness (see for example Photodermatol. Photoimmunol. Photomed., Vol. 7, pp. 153–158, 1990; and J. Photochem. Photobiol. B: Biol., Vol. 9, pp. 323–334, 1991), while retinoic acid can ameliorate such phenomena (see for example J. Invest. Dermatol., Vol.98, pp. 248–254, 1992). However, disadvantageously, these compounds have insufficient effects in vivo, have strong cellular toxicity, or low optical stability. Further, anti-inflammatory agents and retinoic acids also share these adverse effects.

Accordingly, there remains a critical need for the development of an agent for suppressing the activation of inflammatory factor(s), which is particularly great in view of pharmacological activity and safety profile.

SUMMARY OF THE INVENTION

It is an object of the present invention to provide an agent for suppressing the activation of inflammatory factor(s), which is useful and safe for the prevention, amelioration and/or therapeutic treatment of various diseases, such as diseases involved in the activation of inflammatory factor(s) and diseases or dermal damages based on the activation of inflammatory factor(s).

In a preferred object of the present invention is to provide a cystine derivative represented by formula (I):

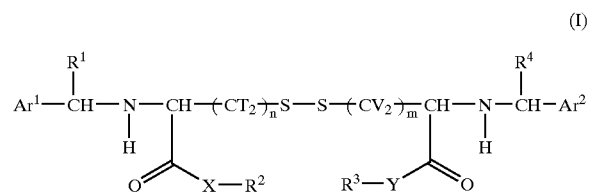

wherein

"n" and "m" independently represent an integer of 0 to 5; $Ar^1$ and $Ar^2$ independently represent a 2-hydroxyaryl group or a heterocycle-containing group, wherein the heterocycle composing the heterocycle-containing group contains a total of 3 to 14 ring atoms including a total of one to 4 heteroatoms independently selected from the group consisting of oxygen, nitrogen and sulfur, wherein the heterocycle may be wholly or partially saturated or aromatic, and wherein the 2-hydroxyaryl group and the heterocycle-containing group may be independently substituted with at least one substituent selected from the group consisting of: halogen atom, hydroxyl group, cyano group, nitro group, amino group, $C_1$–$C_{20}$ alkyl group, $C_1$–$C_4$ alkyl group wherein at least a part of the hydrogen atoms is substituted with fluorine atom(s), $C_1$–$C_6$ alkoxy group, $C_1$–$C_6$ hydroxyalkyl group, and $C_1$–$C_6$ aminoalkyl group;

$R^1$ and $R^4$ independently represent a substituent selected from the group consisting of hydrogen atom, $C_1$–$C_6$ alkyl group, and phenyl group;

X and Y independently represent O or NH;

$R^2$ and $R^3$ independently represent a substituent selected from the group consisting of hydrogen atom, $C_1$–$C_{20}$ alkyl group, $C_7$–$C_{16}$ aralkyl group, and $C_2$–$C_{20}$ unsaturated hydrocarbon group having unsaturated carbon-carbon bond(s) within the molecule; and the two Ts independently represent hydrogen atom or $C_1$–$C_6$ alkyl group and the two Vs independently represent hydrogen atom or $C_1$–$C_6$ alkyl group, and wherein the cystine derivative may be in a form selected from the group consisting of a free form, a salt form and a solvate form; and additionally wherein the cystine derivative may be an optically active substance or a racemic modification.

It is an object of the present invention to provide an agent that suppresses the promotion of free radical generation, in which biological metals (for example, iron) are involved, the expression of inflammatory proteins and the activation of gene transcription regulatory factors involved therein.

It is a further object of the present invention to provide a substance with great physico-chemical properties as the effective ingredient thereof, a method for suppressing the activation of inflammatory factor(s) using such agent for suppressing the activation of inflammatory factor(s), and pharmaceutical agents. In a preferred object of the present invention is to provide external skin application agents, nutrition agents, eye drops and transfusion and the like, cosmetics (including additives for cosmetics), foods or drinks (including health foods or drinks) and the like for suppressing the activation of inflammatory factors.

The above objects highlight certain aspects of the invention. Additional objects, aspects and embodiments of the invention are found in the following detailed description of the invention.

DETAILED DESCRIPTION OF THE INVENTION

Unless specifically defined, all technical and scientific terms used herein have the same meaning as commonly understood by a skilled artisan in organic chemistry, pharmacology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The present invention is based, in part, on the inventor's discovery that the objects of the present invention can be obtained by the synthesis of a novel cystine derivative (not only the free form but also other forms, preferably salts and solvates can be used; particularly preferably, the form of the cystine derivative can be selected from pharmaceutically or cosmetologically acceptable salts, solvates including hydrates and the like) with both of the following formula (I) with a metal coordination function and a disulfide structure. Additionally, the inventors have found that the novel derivative is very great as the effective ingredient for an agent of suppressing the activation of inflammatory factors. Based on these various new findings, the inventors have achieved the present invention.

The invention encompasses the following aspects:
1. A Novel Cystine Derivative and a Method for Producing the Same In one aspect, the present invention relates to a cystine derivative represented by formula (I).

The cystine derivative may be any form of free form, salt and solvate (including hydrate), if any.

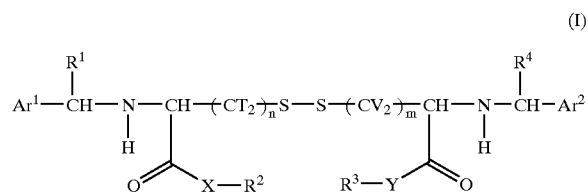

(I)

In the general formula (I), "n" and "m" independently represent an integer of 0 to 5; $Ar^1$ and $Ar^2$ independently represent any of a 2-hydroxyaryl group and a heterocycle-containing group (a heterocyclic ring-containing group).

The heterocycle composing the heterocycle-containing group contains a total of 3 to 14 ring atoms and contains a total of one to 4 heteroatoms (atoms different from the ring atoms), as independently selected from the group consisting of oxygen, nitrogen and sulfur, where the heterocycle may be wholly or partially saturated or aromatic.

The 2-hydroxyaryl group and the heterocycle-containing group may independently contain one or more substituents selected from the following substituents: halogen atom, hydroxyl group, cyano group, nitro group, amino group, $C_1$–$C_{20}$ alkyl group, $C_1$–$C_4$ alkyl group, wherein at least a part of the hydrogen atoms is substituted with fluorine atom(s) (for example, perfluoroalkyl group or the like), $C_1$–$C_6$ alkoxy group, $C_1$–$C_6$ hydroxyalkyl group, and $C_1$–$C_6$ aminoalkyl group.

$R^1$ and $R^4$ independently represent a substituent selected from the group consisting of: hydrogen atom, $C_1$–$C_6$ alkyl group, and phenyl group.

X and Y independently represent any group of O and NH. "O" can be expressed as —O—, while "NH" can be expressed as —NH—.

$R^2$ and $R^3$ independently represent a substituent selected from the group consisting of: hydrogen atom, $C_1$–$C_{20}$ alkyl group, $C_7$–$C_{16}$ aralkyl group, and $C_2$–$C_{20}$ unsaturated hydrocarbon group having (one or a plurality of) unsaturated carbon-carbon bond(s) within the molecule.

The two Ts independently represent hydrogen atom or $C_1$–$C_6$ alkyl group. The two Vs independently represent hydrogen atom or $C_1$–$C_6$ alkyl group.

The cystine derivative may be in any form, such as a free form, a salt form and a solvate form. Further, the cystine derivative may be an optically active substance (L-form, D-form or the like) or a racemic modification. In view of the derivative of naturally occurring cystine, the L form is preferable.

The aspect of the invention is sometimes referred to as "novel cystine derivative of the invention".

In an additional aspect, the invention relates to a method for producing the novel cystine derivative characteristically including at least one process of the following A through C processes.

A. A process including a step of allowing two amino groups in a free amino acid with intramolecular disulfide bond (preferably cystine, homocystine, or penicillamine disulfide) to react with an aldehyde or a ketone (preferably salicylaldehyde, pyridine carboxaldehyde or pyridoxal) to form a Schiff base. In a subsequent step the Schiff base is reduced. In a further step of the a process the resulting compound is subjected to an esterification reaction to esterify the carboxyl group, or alternatively the process includes a step of further introducing a protective group into a substituent requiring the protective group in the compound, a step of carrying out esterification or amidation and a step of removing the protective group.

More specifically, to prepare the compound represented by the general formula (I) by process A, a free amino acid with no substitution in the two carboxyl groups and the two amino groups (preferably cystine, homocystine or penicillamine disulfide) is used as a starting material in the presence of an acid (for example the acid(s) from Lewis acids such as titanium (IV) tetrachloride and trifluoroborane-ether complex, inorganic acids such as hydrochloric acid and sulfuric acid, organic sulfonic acids such as methanesulfonic acid and p-toluenesulfonic acid, or carboxylic acids such as acetic acid and trifluoroacetic acid). If necessary, the starting material is allowed to react with an aldehyde or a ketone (preferably salicylaldehyde, pyridine carboxaldehyde or pyridoxal) to form a Schiff base. The Schiff base is reduced by using a reducing agent (for example, sodium borohydride or sodium triacetoxyborohydride) to introduce one 2-hydroxyarylalkyl group or one heterocycle-containing alkyl group into each of the two amino groups. The process may additionally include a step of esterification or amidation after a protective group is introduced into a substituent requiring the protective group in the resulting compound, and a step of removing the protective group.

B. A process including a step of allowing two free amino groups in a free amino acid with intramolecular disulfide bond, an ester of the amino acid, or an amide form of the amino acid to react with an aldehyde or a ketone (preferably salicylaldehyde, pyridine carboxaldehyde or pyridoxal) to form a Schiff base and a step of reducing the Schiff base, where the amino acid is preferably cystine, homocystine or penicillamine disulfide.

More specifically, to prepare the compound represented by the general formula (I) by process B, a free amino acid without any substitution in the two carboxyl groups and the two amino groups (preferably cystine, homocystine or penicillamine disulfide) is used as the starting material. After the two amino groups are protected, if necessary, followed by esterification or amidation, the protective groups on the amino groups are removed; the resulting compound is allowed to react with an aldehyde or a ketone (preferably salicylaldehyde, pyridine carboxaldehyde or pyridoxal) in the presence of an acid (for example, the acid(s) from Lewis acids such as titanium (IV) tetrachloride and trifluoroborane-ether complex, inorganic acids such as hydrochloric acid and sulfuric acid, organic sulfonic acids such as methanesulfonic acid and p-toluenesulfonic acid, or carboxylic acids such as acetic acid and trifluoroacetic acid), if necessary, to form a Schiff base. The Schiff base is then reduced by using a reducing agent (for example sodium borohydride or sodium triacetoxyborohydride) to introduce one 2-hydroxyarylalkyl group or one heterocycle-containing alkyl group into each of the two amino groups.

C. A process including a step of allowing amino group in a free amino acid with thiol group or protected thiol group, an ester of the amino acid, or an amide form of the amino acid to react with an aldehyde or a ketone (preferably salicylaldehyde, pyridine carboxaldehyde or pyridoxal) to form a Schiff base, a step of reducing the Schiff base and deprotecting the protective group if necessary, and an additional step of forming disulfide bond via oxidation reaction, where the amino acid is preferably cysteine and homocysteine.

More specifically, in process C, the amino group of a free amino acid with thiol group or protected thiol group, an ester of the amino acid or an amide form of the amino acid, where the amino acid is preferably cysteine or homocysteine, is allowed to react with an aldehyde or a ketone (preferably salicylaldehyde, pyridine carboxaldehyde or pyridoxal) in the presence of an acid (for example, the acid(s) from Lewis acids such as titanium (IV) tetrachloride and trifluoroborane-ether complex, inorganic acids such as hydrochloric acid and sulfuric acid, organic sulfonic acids such as methanesulfonic acid and p-toluenesulfonic acid, or carboxylic acids such as acetic acid and trifluoroacetic acid), if necessary, to form a Schiff base. The Schiff base is then reduced by using a reducing agent (for example, sodium borohydride or sodium triacetoxyborohydride) to introduce one 2-hydroxyarylalkyl group or one heterocycle-containing alkyl group into each of the two amino groups. After the protective group is then deprotected, if necessary, disulfide bond is formed via oxidation. The compound represented by the general formula (I) described above can be also prepared by the method as well.

2. Agent for Suppressing the Activation of Inflammatory Factor(s)

In another aspect, the present invention relates to an agent for suppressing the activation of inflammatory factor(s), where the agent contains the inventive cystine derivative represented by formula (I) as an effective ingredient.

The cystine derivative to be used as the effective ingredient in accordance with the invention first includes the free form. The cystine derivative is not limited to the free form. Various forms such as salts and solvates thereof, if any, may be used as the effective ingredient in the invention. The cystine derivative also includes these forms. In the present specification, therefore, the term "cystine derivative" widely includes various forms thereof, such as free form, salts thereof and solvates thereof. The effective ingredient is not necessarily limited to one species. Two or more such effective ingredients may be used as well. Further, substance(s) with an action to suppress the activation of inflammatory factor(s) other than the cystine derivative, for example disulfide derivative(s) and amino acid derivative(s), may be used in combination.

The aspect of the invention is sometimes referred to as "the agent for suppressing the activation of inflammatory factor(s) of the invention" below.

Herein, the cystine derivative to be used as the effective ingredient in the agent for suppressing the activation of inflammatory factor(s) of the invention is a novel compound concurrently having the characteristic structure profiles of disulfide compounds and N-(2-hydroxybenzyl)-amino acid derivatives, having been known to have an anti-inflammation action, and can be used as a greater agent for suppressing the activation of inflammatory factors, which has multiple functions as a single agent for suppressing the activation of inflammatory factors, compared with these existing disulfide compounds and N-(2-hydroxybenzyl)-amino acid derivatives.

3. Use of the Agent for Suppressing the Activation of Inflammatory Factor(s)

In another embodiment, the present invention relates to a use of the agent for suppressing the activation of inflammatory factor(s) in more specific forms for use, namely pharmaceutical agents (including pharmaceutical products, external skin application agents, eye drops, nutrition agents, transfusion and the like), cosmetics (including additives for cosmetics), and foods or drinks (including health foods or drinks). More specifically, the present invention relates to the pharmaceutical agents, cosmetics, foods or drinks and the like, which characteristically contain the cystine derivative for use in the agent for suppressing the activation of inflammatory factor(s) of the invention as an effective ingredient.

Still more specifically, the invention relates to a therapeutic agent for mammals including humans suffering from or being sensitive to diseases involved in the activation of inflammatory factor(s), and an agent for suppressing the activation of inflammatory factor(s), which are to be used in the form of an agent for preventing, ameliorating and/or therapeutically treating inflammatory disorder(s) (disease (s)).

For these uses, various pharmaceutically or cosmetologically acceptable carriers or additives may be admixed with the cystine derivative of formula (I).

The invention in such aspect is sometimes referred to as "the use of the agent for suppressing the activation of inflammatory factor(s) of the invention", in particular, so as to distinguish the use from the agent for suppressing the activation of inflammatory factor(s) of the invention.

4. Method for Suppressing the Activation of Inflammatory Factor(s) or the Like

In an additional embodiment, the present invention relates to a method for using the agent for suppressing the activation of inflammatory factor(s). More specifically, the invention relates to a method for suppressing the activation of inflammatory factor(s), which comprises ingesting or administering to a subject (i.e., mammals including humans) in need thereof, requiring the suppression of the activation of inflammatory factor(s), an effective amount of the cystine derivative (which may be in the free form, a salt thereof or a solvate thereof; one or multiple such derivatives may be used) as the effective ingredient applicable to the method.

Similarly, the invention relates to a method for preventing, ameliorating and/or therapeutically treating disease(s) involved in the activation of inflammatory factor (s), characterized by allowing mammal(s) including human (s) suffering from or being sensitive to the disease(s) to be ingested or administered by the effective amount of the derivative.

Further, the invention relates to a method for preventing, delaying, ameliorating and/or therapeutically treating skin change via aging or aesthetically unfavorable skin change as induced or promoted by inflammatory factor(s), including administering (applying) the cosmetic or external skin application agent containing the derivative as the effective ingredient on the skin of mammals including humans.

The form to be ingested or administered includes the forms of the agent for suppressing the activation of inflammatory factor(s) of the invention.

The agent for suppressing the activation of inflammatory factor(s) can be carried out in any form of pharmaceutical products, foods or drinks and cosmetics, or in a form of the agent as used therein.

The method is particularly preferably used as a method for therapeutically treating, ameliorating and/or preventing disease(s) (disorder(s)) involved in the activation of inflammatory factor(s), or a method for preventing, delaying, ameliorating and/or therapeutically treating skin change via aging or aesthetically unfavorable skin change as induced or promoted by the inflammatory factor(s).

The inventions in these aspects are sometimes individually referred to as the inventions of "the method for suppressing the activation of inflammatory factor(s) of the invention" hereinafter.

5. Use for the Agent for Suppressing the Activation of Inflammatory Factor(s) or the Like In a still additional aspect, the present invention relates to a use of the novel cystine derivative of the invention for the agent for suppressing the activation of inflammatory factor (s).

Examples of the agent for suppressing the activation of inflammatory factor(s) preferably include such agent in any form of pharmaceutical products, foods or drinks or cosmetics, or in any form of the agent used therein.

In the context, the agent for suppressing the activation of inflammatory factor(s) includes the agent for suppressing the activation of inflammatory factor(s) of the invention, as described above.

The agent for suppressing the activation of inflammatory factor(s) is preferably used for therapeutically treating, ameliorating and/or preventing disease(s) (disorder(s)) involved in the activation of inflammatory factor(s) and for preventing, delaying, ameliorating and/or therapeutically treating skin change via aging or aesthetically unfavorable skin change as induced or promoted by the inflammatory factor(s).

The mode for carrying out the invention is now described hereinbelow.

The novel cystine derivative of the invention and the novel cystine derivative for use as the effective ingredient in the agent for suppressing the activation of inflammatory factor(s) of the invention are now described more specifically. The novel cystine derivative is represented by formula (I).

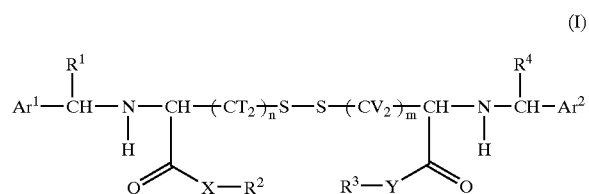

In the formula (I), "n" and "m" independently represent an integer of 0 to 5. In view of production simplicity, "n" and "m" independently represent 1 or 2.

In the general formula (I), the aryl group composing the 2-hydroxyaryl group represented by $Ar^1$ and $Ar^2$ includes for example phenyl group, 1-naphthyl group, 2-naphthyl group and 4-phenyl-phenyl group.

In the general formula (I), the heterocycle composing the heterocycle-containing group represented by $Ar^1$ and $Ar^2$ contains 3 to 14 ring atoms, where one to 4 of the ring atoms are heteroatoms or atoms different from the ring atoms as independently selected from the group consisting of oxygen, nitrogen and sulfur, while the heterocycle may be wholly or partially saturated or aromatic. Examples of the heterocycle-containing group include pyridyl group, quinolinyl group, isoquinolinyl group, pyrazinyl group, indolyl group, imidazolyl group, phenanthrolinyl group, piperidinyl group, piperazinyl group and morpholinyl group. Among these groups, the aryl group composing 2-hydroxyaryl group and the heterocycle composing the heterocycle-containing group preferably include for example phenyl group, 2-naphthyl group, 2-pyridyl group, 3-pyridyl group, 4-pyridyl group, 2-quinolinyl group, 3-quinolinyl group, and 4-quinolinyl group and more preferably include for example phenyl group, 2-naphthyl group, 2-pyridyl group, 3-pyridyl group and 4-pyridyl group.

The hydrogen atom(s) bonded to the 2-hydroxyaryl group and the heterocycle-containing group as described above may satisfactorily be substituted with appropriate substituent(s), unless the substituent(s) adversely affect the action to suppress the activation of inflammatory factor(s) as intended in accordance with the invention. Examples of such substituent(s) include halogen atoms such as fluorine atom, chlorine atom, bromine atom and iodine atom, hydroxyl group, cyano group, nitro group, amino group, C1–C20 alkyl groups, C1–C4 alkyl groups where at least a part of the hydrogen atoms is substituted with fluorine atom(s) (perfluoroalkyl group and the like), C1–C6 alkoxy groups, C1–C6 hydroxyalkyl groups, and C1–C6 aminoalkyl groups.

The alkyl groups with one to 20 carbon atoms include linear alkyl groups, branched alkyl groups and cycloalkyl groups and include for example methyl group, ethyl group, propyl group, isopropyl group, n-butyl group, 2-methylpropyl group, 1-methylpropyl group, 1,1-dimethylethyl group, cyclobutyl group, n-pentyl group, 1-methylbutyl group, 2-ethylpropyl group, 2,2-dimethylpropyl group, 2-methylbutyl group, 3-methylbutyl group, 1,1-dimethylpropyl group, cyclopentyl group, n-hexyl group, cyclohexyl group, n-heptyl group, n-octyl group, 2-ethylhexyl group, nonyl group, 7-methyloctyl group, decyl group, 8-methylnonyl group, undecyl group, dodecyl group, tridecyl group, 11-methyldodecyl group, pentadecyl group, hexadecyl group, heptadecyl group, 15-methylhexadecyl group, octadecyl group, 16-methylheptadecyl group, nonadecyl group, 17-methyloctadecyl group, 11-cyclopentylundecyl group, and 1,1,3,3-tetramethylbutyl group.

The alkyl groups with one to 4 carbon atoms where at least a part of the hydrogen atoms is substituted with fluorine atom(s) (perfluoroalkyl group and the like) include for example trifluoromethyl group, 2,2,2-trifluoroethyl group, heptafluoroethyl group, trifluoromethoxymethyl group, heptafluoropropyl group, heptafluoroisopropyl group, nonafluorobutyl group, nonafluoro-2-methylpropyl group, and nonafluoro-1,1-dimethylethyl group.

The alkoxy groups with one to 6 carbon atoms include for example methoxy group, ethoxy group, isopropoxy group, n-propoxy group, n-butoxy group, 1-methylpropoxy group, 2-methylpropoxy group, 1,1-dimethylethoxy group, cyclobutoxy group, n-pentoxy group, 1-methylbutoxy group, 2-ethylpropoxy group, 2,2-dimethylpropoxy group, 2-methylbutoxy group, 3-methylbutoxy group, 1,1-dimethylpropoxy group, cyclopentoxy group, n-hexyloxy group and cyclohexyloxy group.

The hydroxyalkyl groups with one to 6 carbon atoms include for example hydroxymethyl group, 2-hydroxyethyl group, 3-hydroxypropyl group, 2-hydroxypropyl group, 4-hydroxybutyl group, 5-hydroxypentyl group, and 6-hydroxyhexyl group.

The aminoalkyl groups with one to 6 carbon atoms include for example aminomethyl group, 2-aminoethyl group, 3-aminopropyl group, 2-aminopropyl group, 4-aminobutyl group, 5-aminopentyl group and 6-aminohexyl group.

In the general formula (I), the alkyl group with one to 6 carbon atoms as represented by $R^1$ and $R^4$ includes for example methyl group, ethyl group, propyl group, isopropyl group, n-butyl group, 2-methylpropyl group, 1-methylpropyl group, 1,1-dimethylethyl group, cyclobutyl group, n-pentyl group, 1-methylbutyl group, 2-ethylpropyl group, 2,2-dimethylpropyl group, 2-methylbutyl group, 3-methylbutyl group, 1,1-dimethylpropyl group, cyclopentyl group, n-hexyl group, and cyclohexyl group.

The alkyl group with one to 20 carbon atoms as represented by $R^2$ and $R^3$ in the general formula (I) and examples thereof are the alkyl group with one to 20 carbon atoms as described as one of the possible substituents for the 2-hydroxyaryl group or the heterocycle-containing group and the examples thereof.

The aralkyl group with 7 to 16 carbon atoms as represented by $R^2$ and $R^3$ in the general formula (I) includes for example benzyl group, 2-methoxybenzyl group, 3-methoxybenzyl group, 4-methoxybenzyl group and 2,4-dimethoxybenzyl group.

The unsaturated hydrocarbon group with one or more unsaturated carbon-carbon bonds within the molecule with 2 to 20 carbon atoms as represented by $R^2$ and $R^3$ in the general formula (I) includes for example a linear or branched hydrocarbon group with preferably 2 to 18 carbon atoms, more preferably 5 to 18 carbon atoms, which contains at least one unsaturated carbon-carbon bond (carbon-carbon double bond, carbon-carbon triple bond and the like) within the molecule. For example, the unsaturated hydrocarbon group is an unsaturated hydrocarbon group which may contain one or two or more carbon-carbon double bonds or carbon-carbon triple bonds in some case, including for example vinyl group, ethynyl group, 2-propinyl group, 2-butenyl group, 2-penten-4-ynyl group, 1,4-hexadienyl group, and unsaturated alkyl groups derived from unsaturated fatty acids such as 5-tetradecanyl group, 7-hexadecanyl group, 9-octadecanyl group and 6,9-octadecadienyl group.

In the general formula (I), the two Ts independently represent hydrogen atom or $C_1$–$C_6$ alkyl group, while the two Vs independently represent hydrogen atom or $C_1$–$C_6$ alkyl group. Examples of $C_1$–$C_6$ alkyl group are described as the examples of the alkyl group with one to 6 carbon atoms as represented by $R^1$ and $R^4$.

The cystine derivative may be in any form of free form, salt and solvate. Further, the cystine derivative may be an optically active substance or a racemic modification (racemic compound; racemic mixture or the like).

In case of using the novel cystine derivative as the effective ingredient of the agent for suppressing the activation of inflammatory factor(s) of the invention, only one compound corresponding to the novel cystine derivative specifically described in the invention may be used. Even in case of using only one compound, the compound may be used in plural forms of free form, salt and solvate or may be used in a single form among them, for example the single form of free form. Further, cystine derivatives including plural compounds corresponding to the cystine derivative may appropriately be used in combination. In this case, the individual compounds may be used in plural forms of free form, salt and solvate or may be used in a single form among them, for example the single form of free form.

In accordance with the invention, the term "novel cystine derivative" has a meaning encompassing both single derivative (single compound) and plural derivatives (plural compounds), which are in a single form of free form, salt or solvate and in plural forms of free form, salt and solvate.

As described above, generally, the cystine derivative can be used in the form of free form but may be used in the form of a salt or a solvate, if necessary. Preferably, the salt is appropriately selected from pharmaceutically acceptable salts and cosmetologically acceptable salts.

The solvate is preferably used in a pharmaceutically or cosmetologically acceptable form, for example a hydrate form.

The agent for suppressing the activation of inflammatory factors of the invention is a substance to be used for suppressing the activation of inflammatory factor(s) in mammals, particularly humans. For this purpose, the agent can be used for various uses.

In case of using the agent for suppressing the activation of inflammatory factor(s) of the invention, the agent can be used for any type or any profile of inflammatory factors with no specific limitation. The inflammatory factors typically include for example IL-1α and/or NF-κB.

The salt form is now described more specifically hereinbelow.

The cystine derivative can be used as a pharmaceutically or cosmetologically acceptable acid addition salt thereof, including for example salts with hydrogen halide salt such as hydrochloride salt, hydrobromide salt and hydroiodide salt, and salts with inorganic acids such as nitrate salt, sulfate salt and phosphate salt, salts with organic acids such as methanesulfonate salt, ethanesulfonate salt, benzenesulfonate salt, p-toluenesulfonate salt, 1-camphorsulfonate salt, acetate salt, lactate salt, citrate salt, tartrate salt, succinate salt, maleate salt, fumarate sale, gluconate salt, glycolate salt, saccharin salt, benzoate salt, fatty acid salt, and pyroglutamate, and salts with acidic amino acids such as aspartic acid and glutamic acid.

In case of using the cystine derivative as the effective ingredient of the agent for suppressing the activation of inflammatory factor(s), these salts may be used singly in one salt form or may be used in a combination of two or more of such salts. Additionally, these salts may satisfactorily be used in the form of a mixture of one or more such salts with one free form. In such case, for example, the cystine derivative in the form of an amino acid salt thereof as the effective ingredient as obtained at a separate salt preparation step may be blended. Further, organic acid(s) for example amino acid and the effective ingredient of cystine derivative (free form) may be blended separately to prepare various blend compositions, where objective salts thereof, for example amino acid salt thereof may be formed. Otherwise, such organic acid(s) may be mixed with the free form or the hydrate for use.

The cystine derivative can be used as a pharmaceutically or cosmetologically acceptable base addition salt. For example, salts thereof with alkali metals, such as sodium salt and potassium salt, salts thereof with alkali earth metals such as magnesium and calcium, zinc salt and copper salt, salts thereof with amines such as triethanolamine, salts thereof with basic amino acids such as lysine, arginine, ornithine, histidine, and tryptophan, and salts thereof with various organic bases can be listed. As described above, these may be blended in the form of for example amino acid salt. Otherwise, such amino acid and the free form of the novel cystine derivative of the invention may separately be blended to prepare an objective composition, where the cystine derivative is allowed to form the salt with the amino acid.

In case of using these salts as the effective ingredient of the agent for suppressing the activation of inflammatory factor(s), the salts may be used singly in one salt form or may be used in combination of two or more of such salts or may be used in the form of a mixture of one or more salts thereof with the free form or may be mixed with the free form or the hydrate thereof for use.

The solvent for forming a pharmaceutically or cosmetologically acceptable solvate including the hydrate of the novel cystine derivative of the invention includes for example water, methanol, ethanol, isopropanol, ethyl acetate, and isopropyl acetate. The solvent forming the solvate including hydrate may be used singly or in mixture of two or more of such solvents.

A preferable cystine derivative according to the present invention is the following cystine derivative represented by formula (I), where "n" and "m" both are 1 or 2; both Ts and both Vs are a hydrogen atom or a $C_1$–$C_3$ alkyl group; $R^1$ and $R^4$ both are hydrogen atom, phenyl group or $C_1$–$C_3$ alkyl group; X and Y both are O or NH; $R^2$ and $R^3$ both are hydrogen atom or $C_1$–$C_{20}$ alkyl group; both $Ar^1$ and $Ar^2$ are selected from 2-hydroxyphenyl group, 2-hydroxynaphthyl group, 2-hydroxypyridyl group and pyridyl group, which independently may be substituted with one or more selected from halogen atom, hydroxyl group, nitro group, $C_1$–$C_4$ alkyl group, $C_1$–$C_4$ alkoxy group, $C_1$–$C_3$ hydroxyalkyl group, and $C_1$–$C_3$ aminoalkyl group.

Concerning stereoisomers with no specific limitation, the L form is preferable because cystine derivatives naturally occurring are in L forms.

A more preferable cystine derivative represented by formula (I) is the following, wherein "n" and "m" both are 1 or 2; both Ts and both Vs are hydrogen atom or methyl group; $R^1$ and $R^4$ both are hydrogen atom; X and Y both are O or NH; $R^2$ and $R^3$ both are hydrogen atom or $C_1$–$C_8$ alkyl group; both of $Ar^1$ and $Ar^2$ are selected from 2-hydroxyphenyl group, 2-hydroxynaphthyl group, 2-hydroxypyridyl group and pyridyl group, which independently may or may not be substituted with one or more selected from hydroxyl group, nitro group, $C_1$–$C_4$ alkyl group, $C_1$–$C_4$ alkoxy group, $C_1$–$C_3$ hydroxyalkyl group, and $C_1$–$C_3$ aminoalkyl group.

A still more preferable cystine derivative for the effective ingredient for use in the agent for suppressing the activation of inflammatory factor(s) of the invention is a cystine derivative represented by formula (I), wherein "n" and "m" both are 1 or 2; both Ts and both Vs are hydrogen atom or methyl group; $R^1$ and $R^4$ both are hydrogen atom; X and Y both are O or NH; $R^2$ and $R^3$ both are hydrogen atom or $C_1$–$C_8$ alkyl group; both of $Ar^1$ and $Ar^2$ are selected from 2-hydroxyphenyl group, 2-hydroxypyridyl group and pyridyl group, which independently may be substituted with one or more selected from hydroxyl group, $C_1$–$C_4$ alkyl group, $C_1$–$C_4$ alkoxy group, and $C_1$–$C_3$ hydroxyalkyl group.

The method for producing the novel cystine derivative of the invention is now described below.

For preparation of the novel cystine derivative represented by formula (I) of the invention, the novel cystine derivative can be prepared by conventional methods using, for example, commercially available amino acid derivatives (for example free, amino acids such as cystine, homocystine, and penicillamine disulfide) or salts, esters, or amides thereof as purchased. Purchasing commercially available amino acid derivatives and other raw materials and the like and utilizing the reaction conditions used in methods known as the synthetic methods of these compounds (for example, Protective Groups in Organic Chemistry, the second edition, (John Wiley & Sons, Inc. 1991); Protective Groups in Organic Chemistry, the third edition (John Wiley & Sons, Inc. 1999); Comprehensive Organic Transformations, the second edition (John Wiley & Sons, Inc. 1999)) for conversion of functional group and structural conversion, the objective derivative can readily be obtained.

Among the compounds represented by formula (I), for example, a novel cystine derivative never described in any reference can be obtained by using L-cystine as described above to allow the L-cystine to react with salicylaldehyde to form a Schiff base and reducing the Schiff base using a reducing agent for example sodium borohydride, where "n" and "m" both are 1; the T, V, $R^1$ and $R^4$ are all hydrogen atom; X and Y both are O; $R^2$ and $R^3$ both are hydroxyl group; and $Ar^1$ and $Ar^2$ both are 2-hydroxyphenyl group.

Among the compounds represented by formula (I), for example, a novel cystine derivative never described in any reference can be obtained by using L-cystine dimethyl ester as described above to allow the L-cystine dimethyl ester to react with salicylaldehyde to form a Schiff base and reducing the Schiff base using a reducing agent for example sodium borohydride, where "n" and "m" both are 1; the T, V, $R^1$ and $R^4$ are all hydrogen atom; X and Y both are O; $R^2$ and $R^3$ both are methyl group; and $Ar^1$ and $Ar^2$ both are 2-hydroxyphenyl group.

Among the compounds represented by formula (I), is a novel cystine derivative never described in any reference that can be obtained by using L-cystine as described above to allow the L-cystine to react with salicylaldehyde to form a Schiff base, reducing the Schiff base using a reducing agent for example sodium borohydride and subsequently subjecting the resulting product to oxidation such as oxidation in air or oxidation with iodine, where "n" and "m" both are 1; the T, V, $R^1$ and $R^4$ are all hydrogen atom; X and Y both are O; $R^2$ and $R^3$ both are hydroxyl group; $Ar^1$ and $Ar^2$ both are 2-hydroxyphenyl group.

The agent for suppressing the activation of inflammatory factor(s) of the invention can be used as a therapeutic agent for mammals including humans suffering from or being sensitive to diseases involved in the activation of inflammatory factors or as an agent for preventing, ameliorating and/or therapeutically treating inflammatory diseases, or can be used in the forms of such therapeutic agents. In this case, the agent may contain pharmaceutically or cosmetologically acceptable carrier(s) or additive(s) or the like.

The diseases involved in the activation of inflammatory factors as described above include acute and chronic pains, shock via blood volume decrease, injuries shocks, blood reperfusion disorders, circulative shock, septic shock, systemic inflammation, systemic inflammation syndrome, local inflammation, pneumonia, bronchitis, pancreatitis, cerebral meningitis, encephalitis, ulcerative colitis, inflammatory bowl diseases, dermatitis, nephritis, arthritis, angitis, endocarditis, pleurisy, peritonitis, conjunctivitis, choroiditis, hyperparathyroidism, acne, psilosis, multiple sclerosis, transplant or graft rejection, autoimmune diseases, adult respiratory distress syndrome, osteoarthritis, rheumatoid arthritis, diabetes mellitus, diabetic neuropathy, diabetic renal disorders, diabetic cataract, atopic dermatitis, ileitis, Crohn's disease, asthma, psoriasis, periodontis, apical cyst, nephrosis, central nervous system-demyelinating disorders, glaucoma, cataract, macular degeneration, lupus erythematosus, acquired immunodeficiency syndrome-related dementia, acquired immune deficiency syndrome-related complication, Alzheimer's disease, Huntington's disease, Parkinson's disease, neurodegenerative disease, neuron toxicity, migraine, chemical dependence and narcotics, vomiting, epilepsy, anxiety, memory disorders, depression, hyper kinetic syndrome, emotion disorders, aprosexia, schizophrenia, morphine-induced tolerance and withdrawal symptoms, head injuries, acute spine injuries, thrombosis, platelet coagulation, atherosclerosis, ischemic cardiac diseases, cardiomyopathy, renal failure, glumerulonephritis, anadrenalism, acute pancreatitis, hyperchloresteremia, arteriosclerosis, osteogenic disorder and osteoporosis, bone diseases involved in the increase of bone resorption, pre-eclampsia, eclampsia, uremia complication, chronic liver failure, stroke, cerebral ischemia, cerebral hemorrhage and cancer.

The agent for suppressing the activation of inflammatory factor(s) of the invention may be used in any dosing modes such as oral dosing, parenteral dosing (intravenous dosing and the like), and local dosing.

The agent has great effects on inflammatory diseases induced by ultraviolet ray, in particular.

Furthermore, the agent is preferably used as an eye drops or is preferable for use in the form of eye drops.

The agent for suppressing the activation of inflammatory factor(s) of the invention can be used as cosmetic or external skin application agent or may be used in the form of cosmetic or external skin application agent. Additionally, the agent may be used as additive for cosmetics.

In this case, it is needless to say that the resulting product may contain a carrier or an additive for cosmetics or external skin application agents.

The resulting product can be used for preventing, delaying, ameliorating and/or therapeutically treating skin change via aging or aesthetically unfavorable skin change as induced or promoted by inflammatory factors, preferably when the skin change via aging or the aesthetically unfavorable skin change as induced or promoted by inflammatory factors is skin wrinkle and looseness and/or pigmentation induced or promoted by sunlight, ultraviolet ray in sunlight and/or ultraviolet ray from other light sources.

For the use thereof for such agent for suppressing the activation of inflammatory factors, if necessary, the agent may appropriately contain anti-oxidant(s), anti-inflammatory agent(s), ultraviolet absorbent(s), whitening agent(s), cell activator(s), moisturizing agent(s) and metal chelator(s), the details of which are described below.

The anti-oxidants suitable for use in the present invention include the vitamin A group including retinol, dehydroretinol, retinol acetate, retinol palmitate, retinal, retinoic acid, and vitamin A oil, derivatives thereof and salts thereof, carotenoids such as α-carotene, β-carotene, γ-carotene, cryptoxanthin, astaxanthin, and fucoxanthin, and derivatives thereof, the vitamin B group including pyridoxine, pyridoxal, pyridoxal-5-phosphate ester and pyridoxamine, derivatives thereof and salts thereof, the vitamin C group including ascorbic acid, sodium ascorbate, ascorbic acid stearate, ascorbic acid palmitate, ascorbic acid dipalmitate, and ascorbate magnesium phosphate, derivatives thereof and salts thereof, the vitamin D group including ergocalciferol, cholecalciferol, and 1,25-dihydroxycholecalciferol, derivatives thereof and salts thereof, the vitamin E group including α-tocopherol, β-tocopherol, γ-tocopherol, δ-tocopherol, α-tocotrienol, β-tocotrienol, γ-tocotrienol, δ-tocotrienol, tocopherol acetate, and nicotinate tocopherol, derivatives thereof and salts thereof, trolox, derivatives thereof and salts thereof, dihydroxytoluene, butylhydroxytoluene, butylhydroxyanisole, dibutylhydroxytoluene, α-lipoic acid, dehydrolipoic acid, glutathione, derivatives thereof and salts thereof, erythorbic acids such as uric acid, erythorbic acid and sodium erythorbate, derivatives thereof and salts thereof, gallic acids such as gallic acid and propyl gallate, derivatives thereof and salts thereof, rutins such as rutin and α-glycosyl-rutin, derivatives thereof and salts thereof, tryptophan, derivatives thereof and salts thereof, histidine, derivatives thereof and salts thereof, cysteine derivatives such as N-acetylcysteine, N-acetylhomocysteine, N-octanoylcysteine, and N-acetylcysteine methyl ester and salts thereof, cystine derivatives described in the publication of WO/0021925, such as N,N'-diacetylcystine dimethyl ester, N,N'-dioctanoylcystine dimethyl ester, and N,N'-dioctanoylhomocystine dimethyl ester, and salts thereof, carnosine and derivatives thereof and salts thereof, homocamosine and derivatives thereof and salts thereof, anserine and derivatives thereof and salts thereof, carcinine and derivatives thereof and salts thereof, dipeptide or tripeptide derivatives including histidine and/or tryptophan and/or histamine, and salts thereof, flavonoids such as flavanone, flavone, anthocyanin, anthocyanidine, flavonol, quercetin, quercitrin, myricetin, fisetin, Hamamelis tannin, catechin, epicatechin, gallocatechin, epigallocatechin, epicatechin gallate, and epigallocatechin gallate, tannic acid, caffeic acid, ferulic acid, protocatechuic acid, chalcone, oryzanol, camosol, sesamol, sesamin, sesamolin, zingerone, curcumin, tetrahydrocurcumin, clovamide, deoxyclovamide, shogaol, capsaicin, vanillyl amide, ellagic acid, bromophenol, flavogracin, melanoidin, riboflavin, riboflavin butyrate ester, flavin mononucleotide, flavin adenine nucleotide, ubiquinone, ubiquinol, mannitol, bilirubin, cholesterol, ebselen, selenomethionine, ceruloplasmin, transferrin, lactoferrin, albumin, bilirubin, superoxide dismutase, catalase, glutathione peroxidase, metallothionein, o-phosphono-pyridoxylidene rhodamine, and N-(2-hydroxybenzyl)amino acid described in U.S. Pat. No. 5,594,012, derivatives thereof and salts thereof, and N-(4-pyridoxylmethylene)amino acid, derivatives thereof and salts thereof. If necessary, one or more anti-oxidants can be selected appropriately from these anti-oxidants.

The anti-inflammatory agents suitable for use in the present invention include phenylbutazone, indomethacin, ibuprofen, ketoprofen, allantoin, guaiazulene, resorcin, hydrocortisone, prednisolone, methylprednisolone, dexamethasone, triamcinolone, triamcinolone acetonide, fludoxycortide, clobetasone, clobetasol and esters of these steroids, ketal, acetal and hemiacetal derivatives, flufenamic acid, bufexamac, naploxen, fluviprofen, fenbufen, tenoxicam, piroxicam, mefenamic acid, salicylic acid, salicylate derivatives such as sodium salicylate, methyl salicylate, and glycol salicylate, and salts thereof, D-panthenol and derivatives thereof and salts thereof, glycyrrhizic acid and derivatives thereof and salts thereof, such as glycyrrhizic acid, methyl glycyrrhizinate, and dipotassium glycyrrhizinate, glycyrrhetinic acid and derivatives thereof and salts thereof, such as, glycyrrhetinic acid, glyceryl glycyrrhate, stearyl glycyrrhate and glycyrrhetinyl stearate, chondroitin sulfuric acid and salts thereof, ε-aminocaproic acid, sodium diclofenac, tranexamic acid, diphenhydramine hydrochloride, chlorpheniramine maleate, ichthammol, γ-oryzanol, thianthol, sodium copper chlorophyllin, Angelica keiskei extract, Arnica Montana flower extract, aloe extract, Bistorda extract, Curcuma extract, Hypericum extract, German chamomile extract, Hemerocallis extract, lonicerae extract, Nasturtium officinale extract, Symphytum officinale extract, Acanthopanacis cortex extract, Salvia officinale extract, Lithospermum root extract, Perilla extract, Betula extract, tea extract, Angelica radix extract, Calendula officinalis flower extract, elderberry extract, typhae pollen extract, Sapindus extract, Artemisia extract, eucalyptus extract, Astragalus extract, and zinc oxide. If necessary, one or more anti-inflammatory agents can be selected appropriately from such anti-inflammatory agents.

The ultraviolet absorbents suitable for use in the present invention include for example cinnamic acid-based ultraviolet absorbents such as p-methoxycinnamate-2-ethylhexyl, isopropyl p-methoxycinnamate, sodium p-methoxycinnamate, potassium p-methoxycinnamate, p-methoxycinnamate-2-ethoxyethyl, p-methoxyhydrocinnamate diethanolamine salt, di-p-methoxycinnamate-mono-2-ethylhexanoate glyceryl, octyl methoxycinnamate and methyl diisopropylcinnamate, benzophenone-based ultraviolet absorbents such as 2-hydroxy-4-methoxybenzophenone, 2-hydroxy-4-methoxybenzophenone-5-sulfuric acid, 2-hydroxy-4-methoxybenzophenone-5-sulfate sodium, dihydroxybenzophenone, 2,4-dihydroxybenzophenone, 2,2'-dihydroxy-4,4'-dimethoxybenzophenone, 2,2'-dihydroxy-4-methoxybenzophenone, dihydroxydimethoxybenzophenonesulfate sodium, 2,2',4,4'-tetrahydroxybenzophenone, and 2-hydroxy-4-n-octoxybenzophenone, benzoic acid-based ultraviolet absorbents such as p-aminobenzoic acid, sodium p-aminobenzoate, ethyl p-aminobenzoate, butyl p-aminobenzoate, p-dimethylaminobenzoate-2-ethylhexyl, amyl p-dimethylaminobenzoate, glyceryl p-aminobenzoate, and amyl p-aminobenzoate, salicylic acid-based ultraviolet absorbents such as salicylate-2-ethylhexyl, salicylate triethanolamine, homomenthyl salicylate, salicylate dipropylene glycol, methyl salicylate, salicylate ethylene glycol, phenyl salicylate, amyl salicylate, benzyl salicylate, isopropylbenzyl salicylate, myristyl salicylate, and potassium salicylate, dibenzoylmethane-based ultraviolet absorbents such as 4-tert-butyl-4'-methoxydibenzoylmethane, 4-isopropyldibenzoylmethane, 4-methoxydibenzoylmethane, and 4-tert-butyl-4'-hydroxydibenzoylmethane, urocanic acid-based ultraviolet absorbents such as urocanic acid, and ethyl urocanate, menthyl-O-aminobenzoate, 2-phenyl-benzimidazole-5-sulfuric acid, 2-phenyl-5-methylbenzoxazole, 3-(4-methylbenzylidene)camphor, 2-ethylhexyl-2-cyano-3,3'-diphenyl acrylate, 2-ethyl-2-cyano-3,3'-diphenyl acrylate, 2-(2'-hydroxy-5-methylphenyl)benzotriazole, methyl anthranilate, ethyl anthranilate, menthyl anthranilate, 2,4,6-tris[4-(2-ethylhexyloxycarbonyl)anilino]-1,3,5-triazine, 3,3'-(1,4-phenylenedimethylidene)bis(7,7-dimethyl-2-oxo-bicyclo[2.2.1]heptane-1-methanesulfonic acid) (Mexoryl SX), titanium oxide, zirconium oxide, cerium oxide, and zinc oxide. If necessary, one or more ultraviolet absorbents can be selected appropriately from such ultraviolet absorbents.

The whitening agents suitable for use in the present invention include tyrosinase inhibitors, endothelin antagonists, α-MSH inhibitors, glabridin, glabrene, liquiritin, isoliquiritin, ellagic acid, derivatives thereof and salts thereof, kojic acid, derivatives thereof and salts thereof, hydroquinone such as arbutin, derivatives thereof and salts thereof, cysteine, derivatives thereof and salts thereof, the vitamin C group including ascorbic acid, sodium ascorbate, stearate ascorbyl, palmitate ascorbyl, dipalmitate ascorbyl, and ascorbate magnesium phosphate, and derivatives thereof and salts thereof, glutathione, derivatives thereof and salts thereof, resorcin, derivatives thereof and salts thereof, neoagarobiose, agarose oligosaccharide, asparagus extract, Althaea officinalis root extract, Bistorta extract, Artemisiae Capillaris Spica extract, Pisum bean extract, rose fruit extract, Scutellaria root extract, Ononis spinosa root extract, seaweed extract, Urtica extract, Hemerocallis extract, Rubus extract, Sophora root extract, unrefined sugar extract, extract of Millettia reticulata Benth. and Mucuna birdwoodiana Tutcher, Gokahi (dried Acanthopanax gracilistylus W. W. Smith) extract, wheat germ extract, Asiasari Radix extract, crataegus extract, Cassia mimosoides L. extract, peony root extract, white lily extract, Inulae Flos. Extract, Mori cortex extract, soybean extract, placenta extract, Araliae cortex extract, tea extract, Angelica radix extract, molasses extract, Rosa multiflora Thunb. extract, Amypelopsis japonica Makino extract, grape seed extract, Fagus extract, Flodemannita extract, hops extract, extract of rosa rugosae flos, Japanese dwarf quince, Saxifraga stromifera meerburg extract, Coix seed extract, and momordicae fructus extract. If necessary, one or more whitening agents can be selected appropriately from such whitening agents.

The cell activators suitable for use in the present invention include nucleic acid-related substances such as deoxyribonucleic acids and salts thereof, adenylic acid derivatives and salts thereof, ribonucleic acids and salts thereof, cyclic AMP, cyclic GMP, flavin adenine nucleotide, guanine, adenine, cytosine, thymine, xanthine, caffeine, and theophylline, derivatives thereof and salts thereof, the vitamin A group including retinol, dehydroretinol, retinol acetate, retinol palmitate, retinal, retinoic acid, and vitamin A oil, derivatives thereof and salts thereof, carotenoids such as α-carotene, β-carotene, γ-carotene, cryptoxanthin, astaxanthin, and fucoxanthin, and derivatives thereof and salts thereof, the vitamin B group including pyridoxine, pyridoxal, pyridoxal-5-phosphate ester and pyridoxamine, derivatives thereof and salts thereof, the vitamin C group including ascorbic acid, sodium ascorbate, stearate ascorbyl, palmitate ascorbyl, dipalmitate ascorbyl, and ascorbate magnesium phosphate, derivatives thereof and salts thereof, the vitamin D group including ergocalciferol, cholecalciferol, and 1,25-dihydroxy-cholecalciferol, derivatives thereof and salts thereof, the vitamin E group including α-tocopherol, β-tocopherol, γ-tocopherol, δ-tocopherol, α-tocotrienol, β-tocotrienol, γ-tocotrienol, δ-tocotrienol, acetate tocopherol, and nicotinate tocopherol, derivatives thereof and salts thereof, trolox, derivatives thereof and salts thereof, hinokitiol, cepharanthine, α-linolenic acid, γ-linolenic acid, eicosapentaenoic acid, derivatives thereof and salts thereof, organic acids selected from glycolic acid, succinic acid, lactic acid, and salicylic acid, derivatives thereof and salts thereof, estradiol and derivatives thereof and salts thereof, silk protein and decomposition products thereof, or derivatives thereof, hemoglobin or decomposition products thereof, lactoferrin or decomposition products thereof, animal-derived extracts such as royal jelly, placenta extract, calf blood extract solution, serum protein-free extract, spleen extract, egg ingredients, cock's crest extract, shell extract, shell fish meat extract, Mollusca extract, and fish meat extract, extracts from microorganisms such as fermentation products and metabolic products, asparagus extract, apricot extract, ginkgo extract, phellodendron extract, barley extract, Panax ginseng extract, orange extract, Actinidia chinensis extract, cucumber extract, shiitake extract, Equisetum extract, swertia extract, jujube extract, pepper extract, Calendula officinalis flower extract, carrot extract, garlic extract, hoelen extract, grape seed extract, Fagus bud extract, peach extract, eucalyptus extract, Polyporales ganoderma extract, lettuce extract, lemon extract, and rosemary extract. If necessary, one or more cell activators can be selected appropriately from these cell activators.

The moisturizing agents suitable for use in the present invention include mucopolysaccharides or salts thereof, proteins or decomposition products thereof, and derivatives thereof and salts thereof, soybean or egg-derived phospholipid, glycolipid, ceramide, mucin, honey, erythritol, sugars such as maltose, maltitol, xylitol, xylose, pentaerythritol, fructose and dextrin, and derivatives thereof, acidic polysaccharides such as hyaluronic acid, amino acids and derivatives thereof and salts thereof, such as urea, asparagine, aspartic acid, alanine, arginine, isoleucine, ornithine, glutamine, glycine, glutamic acid, cysteine, cystine, citrulline, threonine, serine, tyrosine, tryptophan, theanine, valine, histidine, hydroxylysine, hydroxyproline, pyrrolidonecarboxylic acid, proline, phenylalanine, methionine, and lysine, D-panthenol, whey protein, Angelica keiskei extract, avocado extract, almond extract, Althaea officinalis root extract, Arnica montana flower extract, aloe extract, strawberry extract, locust extract, rice extract, Artemisiae Capillaris Spica extract, fennel extract, turmeric extract, Malva sylvestris extract, Perilla extract, Scutellaria root extract, Coptis rhizome extract, Lamiaceae lamium extract, Ononis spinosa root extract, olive oil, seaweed extract, cacao butter, German chamomile extract, Avena extract, Garcinia Cambodia extract, Haemerocallis extract, Rubus extract, Hedera extract, lonicerae extract, gardenia extract, Sasa extract, grape fruit extract, Sophora root extract, Nasturtium officinale extract, gentiana extract, geranium extract, Arctium extract, Clematis apiifolia extract, sesame extract, wheat extract, Symphytum officinale extract, Asiasarum root extract, Cactales extract, Saponaria officinalis L. extract, Salvia extract, Crataegus extract, Butyro spermum parkii extract, Perilla extract, Rhemannia root extract, Spiraea extract, peony root extract, ginger extract, Betula extract, Malva extract, Cinidium rhizome extract, Mori cortex extract, soybean extract, Thymus vulgaris extract, tea extract, camellia extract, Angelica radix extract, corn extract, plant worms extract, houttuynie en coeur extract, tormentilla extract, Lupinus extract, Ophiopogon tuber extract, parsley extract, Mentha extract, green Mentha extract, western Mentha extract, Hamamelis extract, rose extract, hinoki extract, sunflower extract, grape extract, Butchers bloom extract, prune extract, Luffa extract, Tilia extract, Paeonia extract, hops extract, jojova oil, borage extract, macadamia nut extract, pine extract, Cydonia oblonga extract, Aesculus hippocastanum extract, Sapindus extract, Lithospermum extract, meadowhome oil, melissa oil, Rodgersia extract, Saxifraga stromifera meerburg extract, Chinese lemon extract, lily extract, Coix seed extract, lime extract, momordicae fructus, lavender extract, apple extract, Gentiana extract, Astragalus extract, Sanguisorba extract, alkali simple thermal spring, and deep water. If necessary, one or more moisturizing agents can be selected appropriately from such moisturizing agents.

The metal chelators suitable for use in the present invention include malic acid, citric acid, salicylic acid, tartaric acid, gluconic acid, phytic acid, derivatives thereof and salts thereof, ethylenediaminetetraacetic acid, derivatives thereof and salts thereof, diethylenetriaminepentaacetic acid, derivatives thereof and salts thereof, N-carboxymethyl-aspartic acid, derivatives thereof and salts thereof, N-carboxymethyl-glutamic acid, derivatives thereof and salts thereof, N,N-bis(carboxymethyl)-aspartic acid, derivatives thereof and salts thereof, N,N-bis(carboxymethyl)-glutamic acid, derivatives thereof and salts thereof, N,N-bis(succinate)-ethylenediamine, derivatives thereof and salts thereof, desfferioxamine, o-phenanthroline, transferrin, ferritin, lactoferrin, caffeic acid, maltol, purpurogalin, pyrogallol, polyphosphate sodium, sodium metaphosphate, and hexametaphosphate sodium. If necessary, one or more metal chelators can be selected appropriately from such metal chelators.

The agent for suppressing the activation of inflammatory factor(s) of the invention may be provided in the form of food or drink (health food and the like), nutrition agent or infusion (transfusion) dosage form.

The amount of the cystine derivative as the effective ingredient of the agent for suppressing the activation of inflammatory factor(s) to be dosed to mammals including humans requiring the agent for suppressing the activation of inflammatory factors is selected appropriately, depending on the type of a disease to be treated and the object for use, the symptom of a patient to be dosed or the dosing mode or the like. When N,N'-bis(2-hydroxybenzyl)-L-cystine is to be dosed as an external skin application agent to humans to coat the skin surface, the L-cystine derivative can be administered at a dose of preferably about (approximately) 1 mg to 2,500 mg per day, more preferably about (approximately) 10 mg to 1,000 mg per day, and still more preferably about (approximately) 50 mg to 500 mg per day. For oral dosing, about the same dose as the amount of the effective ingredient in the external skin application agent per day can be used in the form of a therapeutic agent, a nutrition agent or a food or drink. For parenteral dosing via injections, alternatively, a dose about ½-fold to 1/20-fold the dose of the external skin application agent per day can be used.

For preparation of a dosage form, the dosage form can be prepared by using additives and formulation agents selected for individual purposes.

The method for suppressing the activation of inflammatory factor(s) as well as the method how to use the agent for suppressing the activation of inflammatory factor(s), in particular is now described below.

The cystine derivative represented by formula (I) as the effective ingredient to be used for the method of the invention can be used in the aforementioned various dosage forms for oral or parenteral dosing, if necessary. However, preferably, the cystine derivative is directly dosed to an inflammatory factors activation system. Generally, the cystine derivative is preferably used in the form of a blend with the pharmaceutical agents (therapeutic agent, external skin application agent and the like) or cosmetics. Furthermore, the method of the invention includes a method for preventing, delaying, ameliorating and/or therapeutically treating inflammation or skin change induced by inflammatory factors or skin inflammation, wrinkles or looseness induced by ultraviolet ray. The method includes directly coating the cystine derivative as the effective ingredient of the invention in the form of a pharmaceutical agent (therapeutic agent, preventive agent, external skin application agent and the like) or in the form of a cosmetic on normal skin or at intended sites such as sites in progress of skin change or of the occurrence of inflammation, wrinkles or looseness or at sites under progress thereof.

When the cystine derivative is to be used for blending in therapeutic agents or external skin application agents for the purpose of therapeutically treating, preventing or ameliorating inflammatory disorders, for example, the amount thereof in blend is preferably about 0.01 to 50% by weight, more preferably about 0.1 to 20% by weight, appropriately. When the cystine derivative is to be blended in a cosmetic as an effective ingredient of the prevention and amelioration of inflammatory skin injuries and/or aesthetically unfavorable change, furthermore, the cystine derivative is appropriately blended at about 0.001 to 10% by weight, preferably about 0.1 to 5% by weight. Below 0.001% by weight, the potency thereof for suppressing the activation of inflammatory factors cannot be sufficiently exerted, unpreferably. Above 50% by weight, alternatively, the resulting agent disadvantageously causes problematic touch during use on skin, such as poor spreadability on skin.

Concerning the use of the pharmaceutical agents, cosmetics and the like of the invention and with respect to the long-term dosing and/or coating thereof, the pharmaceutical agents, cosmetics and the like are preferably dosed continuously for at least one month or longer. For the prevention of skin injuries or disorders via the activation of inflammatory factors, the pharmaceutical agents, cosmetics and the like are dosed and/or coated for three months up to the whole life. For the therapeutic treatment of skin injuries or disorders via the activation of inflammatory factors to amelioration, preferably, the pharmaceutical agents, cosmetics and the like are dosed and/or coated over three months to 10 years.

When the cystine derivative is to be blended and used as the effective ingredient in accordance with the invention in the agent for suppressing the activation of inflammatory factor(s) of the invention, particularly in therapeutic agents, eye drops, preventive agents, external skin application agents or cosmetics as the uses thereof, ingredients for general use in therapeutic agents, eye drops, preventive agents, external skin application agent or cosmetics, particularly effective ingredients, carriers, additives and the like can be added within a range with no suppression of the object or advantage of the invention.

Ingredients for general use in therapeutic agents, eye drops, preventive agents, external skin application agents or cosmetics include for example oily raw materials, surfactants, solvents, polymer substances, powder substances, dyes, perfume, and transcutancous absorption-promoting agents.

The oily raw materials suitable for use in the present invention include fats and oils such as animal and vegetable oils, waxes such as lanolin, hydrocarbons such as paraffin, higher alcohols such as cetanol, higher fatty acids such as stearic acid, phospholipids such as sterols and lecithin, synthetic esters such as those from myristic acid and the like, metal soaps, silicone oil, perfluoropolymers, and perfluoropolyethers.

The surfactants suitable for use in the present invention include anionic surfactants, cationic surfactants, amphiphilic surfactants, nonionic surfactants, emulsifiers, and solubilizers.

The solvents suitable for use in the present invention include lower alcohols such as ethanol, ethers, glycerins, liquid nonionic surfactants, liquid oily raw materials, other organic solvents, and water.

The polymer substances suitable for use in the present invention include polyamino acids such as polyaspartic acid, $\epsilon$-polylysine, and $\gamma$-polyglutamic acid, and derivatives thereof, naturally occurring polymer compounds such as collagen and elastin, semi-synthetic polymer compounds such as partially deacetylated chitin, and synthetic polymer compounds such as carboxymethyl cellulose.

The powder substances suitable for use in the present invention include inorganic pigments such as talc, functional pigments such as synthetic mica, particulate composite powders (hybrid fine powders), pearl-gloss pigments such as titanium dioxide-coated mica, photochromic pigments, polymer powders such as nylon powder, and organic powders such as N-$\epsilon$-lauroyl lysine.

The dyes suitable for use in the present invention include Tar Dye Group I designated by law, Tar Dye Group II designated by law, Tar Dye Group III designated by law, wool dyes, natural dyes, and mineral dyes.

The perfume suitable for use in the present invention includes perfume from animals such as musk, perfume from plants such as jasmine, synthetic perfume such as $\alpha$-amylcinnamaldehyde, and composite perfume.

The transcutaneous absorption-promoting agents suitable for use in the present invention include urea, 2-pyrrolidone, 1-hexanol, 1-octanol, 1-decanol, 1-menthol, sodium laurylsulfate, myristate isopropyl, acetate n-hexyl, and oleic acid.

When the agent for suppressing the activation of inflammatory factor(s) of the invention and the specific uses thereof, particularly pharmaceutical agents (therapeutic agent, preventive agent, external skin application agent and the like) or cosmetics are to be prepared, the preparative forms (dosage forms) thereof are not specifically limited but include appropriate dosage forms for example liquid, paste, gel, solid and powder. Further, the cosmetics and external skin application agents of the invention can be used as oil, lotion, cream, emulsion, gel, shampoo, hair rinse, hair conditioner, enamel, foundation, lip stick, solid powder, pack, ointment, tablet, injection, granule, capsule, perfume, powder, eau de Cologne, dental paste, soap, aerosol, and cleansing foam, and additionally as skin aging-preventing and ameliorating agent, dermatitis-preventing and ameliorating agent, bathing agent, hair growth agent, skin tonic, sunburn-preventing agent, prevention and amelioration agent of photo-hypersensitivity such as xeroderma pigmentosum and sunlight allergy, prevention and amelioration agent of photoallergy, prevention and amelioration agent of photo-suppression of immunity, or prevention and amelioration agent of rough skin such as injuries, cracks and chaps.

Additionally, they can be used as therapeutic agents, preventive agents or amelioration agents of various diseases involved in the activation of inflammatory factors, such as acute and chronic pains, shock via blood volume decrease, injuries shocks, blood reperfusion disorders, circulative shock, septic shock, systemic inflammation, systemic inflammation syndrome, local inflammation, pneumonia, bronchitis, pancreatitis, cerebral meningitis, encephalitis, ulcerative colitis, inflammatory bowl diseases, dermatitis, nephritis, arthritis, angitis, endocarditis, pleurisy, peritonitis, conjunctivitis, chorioiditis, hyperparathyroidism, acne, psilosis, multiple sclerosis, transplant or graft rejection, autoimmune diseases, adult respiratory distress syndrome, osteoarthritis, rheumatoid arthritis, diabetes mellitus, diabetic neuropathy, diabetic renal disorders, diabetic cataract, atopic dermatitis, ileitis, Crohn's disease, asthma, psoriasis, periodontis, apical cyst, nephrosis, central nervous system-demyelinating disorders, glaucoma, cataract, macular degeneration, lupus erythematosus, acquired immunodeficiency syndrome-related dementia, acquired immune deficiency syndrome-related complication, Alzheimer's disease, Huntington's disease, Parkinson's disease, neurodegenerative disease, neuron toxicity, migraine, chemical dependence and narcotics, vomiting, epilepsy, anxiety, memory disorders, depression, hyper kinetic syndrome, emotion disorders, aprosexia, schizophrenia, morphine-induced tolerance and withdrawal symptom, head injuries, acute spine injuries, thrombosis, platelet coagulation, atherosclerosis, ischemic cardiac diseases, cardiomyopathy, renal failure, glumerulonephritis, anadrenalism, acute pancreatitis, hyperchloresteremia, arteriosclerosis, osteogenic disorder and osteoporosis, bone diseases involved in the increase of bone resorption, pre-eclampsia, eclampsia, uremia complication, chronic liver failure, stroke, cerebral ischemia, cerebral hemorrhage and cancer.

For the purpose of dosing to animals including humans requiring the prevention, amelioration and/or therapeutic treatment of the various diseases, still additionally, the agent for suppressing the activation of inflammatory factor(s) of the invention can be dosed and/or coated in combination with other pharmaceutical agents for the purpose of the prevention, amelioration and/or therapeutic treatment thereof.

Further, other pharmaceutical agents for the purpose of the prevention, amelioration and/or therapeutic treatment thereof together used with the agent for suppressing the activation of inflammatory factor(s) of the invention may be added to the agent for suppressing the activation of inflammatory factor(s), particularly the therapeutic agents, the eye drops or the cosmetics, or the like. In this case, other pharmaceutical agents which may be added to the therapeutic agents, the eye drops or the cosmetics, or the like may preferably include for example anti-hypertensive agent, anti-depression agent, anti-anxiety agent, anti-atherosclerosis agent, anti-coagulation agent, anti-convulsion agent, congestion-reducing agent, anti-histamine agent, anti-tussive agent, anti-psychotic agent, cognition-enhancing agent, cholesterol biosynthesis inhibitor, cholesterol absorption inhibitor, anti-obesity agent, autoimmune disorders-treating agent, sex function impairment-ameliorating agent, anti-microbial agent and anti-fungal agent, hypnotic agent, anti-Parkinsonism agent, antibiotics, anti-viral agent, anti-cancer agent, barbiturate, sedation agent, nutrition agent, beta blocker, emetic agent, antiemetic agent, diuretic, anti-coagulant, cardiac agent, androgen, corticoid, protein anabolic agent, nitrogen oxide synthesis enzyme (NOS) inhibitor, matrix metalloproteinase inhibitor, cyclooxygenase inhibitor, tumor necrosis factor (TNF) generation inhibitor, anti-infection agent, coronary vasodilator, carbonate dehydratase inhibitor, anti-protozoan agent, gastrointestinal agent, serotonin antagonist, anesthetic agent, blood glucose-decreasing agent, dopaminergic agent, anti-Alzheimer agent, anti-ulcer agent, platelet inhibitor and glycogen phosphorylase inhibitor.

Still furthermore, other routine ingredients for use in the inventive preventive agents, therapeutic agents, eye drops, external skin application agents or cosmetics can be added to the agent for suppressing the activation of inflammatory factor(s) of the invention, and particularly to the specific uses thereof, namely preventive agents, therapeutic agents, eye drops, external skin application agents or cosmetics, or the like within a range not suppressing the advantage of the invention. Such other routine ingredients for use in preventive agents, therapeutic agents, eye drops, external skin application agents or cosmetics include for example preservatives and sterilizing agents, browning-preventing agents, buffers, pharmaceutical agents for acne, dandruff and itching-preventing agents, anti-perspiration deodorants, pharmaceutical agents for burn, anti-mite and anti-louse agents, keratin-softening agents, pharmaceutical agents for xerosis, anti-viral agents, hormones, vitamins, amino acids and peptides, proteins, astringent agents, refreshing and stimulating agents, components derived from animals and plants, antibiotics, anti-fungal agents, and hair-growth agents.

In another aspect as described above, the present invention relates to the use of the novel cystine derivative of the invention (active ingredient) for the agent for suppressing the activation of inflammatory factors.

Having generally described this invention, a further understanding can be obtained by reference to certain specific examples, which are provided herein for purposes of illustration only, and are not intended to be limiting unless otherwise specified.

EXAMPLES

Herein below, the blend amount is expressed in % by weight (wt %) in these examples.

Synthetic Example 1

Synthesis of N,N'-bis(2-hydroxybenzyl)-L-cystine

L-Cystine (5.02 g) and aqueous 4 mol/l sodium hydroxide solution (10.4 ml) were added to water (90 ml), to prepare a homogenous solution. Salicylaldehyde (4.45 ml) was added to the resulting solution and the solution was agitated at ambient temperature for 2 hours. The resulting mixture was cooled in an ice bath, followed by addition of sodium borohydride (1.57 g) and agitated under ice cooling for 2 hours. The temperature of the resulting reaction solution was increased to ambient temperature and the reaction solution was agitated overnight.

A sufficient quantity of 6 mol/l hydrochloric acid was added to the reaction solution to adjust the pH of the reaction solution to pH 2 and the solution was agitated at ambient temperature for 30 minutes. To the resulting solution an aqueous 25 wt % sodium hydroxide solution was added to adjust the pH of the reaction solution to pH 5. Subsequently, the resulting solution was agitated at ambient temperature for 30 minutes. The precipitated crystal was separated and dried to recover a crude crystal of N,N'-bis(2-hydroxybenzyl)-L-cystine (7.20 g). A part (2.00 g) of the crude crystal was suspended in methanol (40 ml) and agitated at ambient temperature for 1.5 hours. The resulting crystal was separated and dried to recover N,N'-bis(2-hydroxybenzyl)-L-cystine in a pure crystal form (1.72 g).

The N,N'-bis(2-hydroxybenzyl)-L-cystine obtained by the foregoing method is a novel compound that has never been described in any reference. The spectra data for this compound is shown below:

(NMR analysis)

$^1$H-NMR ($D_2O$+NaOD, 400 MHz) δppm: 3.02 (d, J=4.0 Hz 2H), 3.48 (t, J=4.0 Hz 1H), 3.60 (d, J=12.0 Hz 1H), 3.73 (d, J=12.0 Hz 1H), 6.55–6.63 (m, 2H), 7.07–7.17 (m, 2H).

(Mass analysis)

Mass spectrum m/e: 451.13 (M−H$^-$)

Test Example 1

Test of the Potency of NF-κB Activation Suppression

Test compounds shown in Table 1 were added individually to human epidermal cells at confluency in a culture plate. 18 hours later, the culture broth was exchanged with a phenol red-free culture medium. Using Dermalei M-DMR-80 (manufactured by Toshiba Medical Supplies, Co., Ltd.), the cells were irradiated with an ultraviolet ray (UVB: 50 mJ/cm$^2$). 4 to 5 hours later, the cells were recovered and the nuclear protein was extracted using a general method. By using a gel shift assay method, the activated NF-κB in the resulting nuclear protein was detected. Determination of NF-κB was conducted based on counting the radioactivity of labeled NF-κB using a bioimaging analyzer BAS2000 (manufactured by Fuji Film Co., Ltd.). The ratio of NF-κB activation suppression by the inventive compounds compared with a test compound was calculated by the following formula (1). The results are shown in Table 1.

$$\text{Ratio (\%) of NF-κB activation suppression} = [1-(A1-A3)/(A2-A3)] \times 100 \quad (1)$$

A1: radioactivity of NF-κB band with addition of test compound

A2: radioactivity of NF-κB band without addition of test compound

A3: radioactivity of NF-κB band without addition of test compound and without ultraviolet irradiation

TABLE 1

Test of potency of NF-κB activation suppression

| Test compound | Concentration (mM) | Suppression ratio (%) |
|---|---|---|
| N,N'-Bis(2-hydroxybenzyl)-L-cystine (inventive product) | 0.1<br>0.5<br>1.0 | 41<br>86<br>>100 |
| N,N'-Diacetyl-L-cystine (control product) | 10<br>30 | 48<br>67 |
| N-(2-Hydroxybenzyl)-L-serine (control product) | 10<br>30 | 17<br>34 |

As shown in Table 1, the novel cystine derivatives of the present invention have the potency of NF-κB activation suppression which is the same or better than that of N,N'-diacetyl-L-cystine or N-(2-hydroxybenzyl)-L-serine (known NF-κB activation suppressors). Therefore, due to the intimate relationship between NF-κB activation suppression and activation of inflammatory factors, it is understood that the novel cystine derivatives of the invention also have great inflammatory factor activation suppression potency. Thus, the novel cystine derivatives are very useful as an effective ingredient of an agent for suppressing activation of inflammatory factors.

In case of using the agent for suppressing the activation of inflammatory factor(s) of the invention, various dosage forms of the preparation can be selected. The blend examples 1 to 16 thereof are shown below. These dosage forms were prepared by general methods. Herein, the blend amount was expressed in % by weight (wt %).

| Blend Example 1 Tablet | |
|---|---|
| N,N'-Bis(2-hydroxybenzyl)-L-cystine | 10% |
| Lactose | 50% |
| Starch | 20% |
| Carboxymethyl cellulose | 19% |
| Magnesium stearate | 1% |

| Blend Example 2 Injection | |
|---|---|
| N,N'-Bis(2-hydroxybenzyl)-L-cystine | 0.1% |
| Glucose | 2.0% |
| Water for injections | balance |

| Blend Example 3 Ointment | |
|---|---|
| N,N'-Bis(2-hydroxybenzyl)-L-cystine | 1.0% |
| Urea | 20.0% |
| White Vaseline | 15.0% |
| Light fluid paraffin | 6.0% |
| Cetanol | 3.0% |
| Stearyl alcohol | 3.0% |
| Glyceryl monostearate | 5.0% |
| Perfume | appropriate amount |
| Preservative | appropriate amount |
| Buffer | 1.0% |
| Distilled water | balance |

| Blend Example 4 Skin Lotion | |
|---|---|
| N,N'-Bis(2-hydroxybenzyl)-L-cystine | 3.0% |
| Glycerin | 3.0% |
| Sorbitol | 2.0% |
| Polyoxyethylene (20) oleyl ether | 1.0% |
| Ethanol | 15.0% |
| p-Phenolsulfonate zinc | 0.2% |
| Buffer | 0.1% |
| Perfume | 0.2% |
| Preservative | appropriate amount |
| Distilled water | balance |

| Blend Example 5 Lotion | |
|---|---|
| N,N'-Bis(2-hydroxybenzyl)-L-cystine | 0.5% |
| Glycerin | 4.0% |
| Kaolin | 1.0% |
| Calamine | 0.7% |
| Camphor | 0.2% |
| Ethanol | 14.0% |
| Perfume | appropriate amount |
| Distilled water | balance |

| Blend Example 6 Cream | |
|---|---|
| N,N'-Bis(2-hydroxybenzyl)-L-cystine | 1.0% |
| Kojic acid | 1.0% |
| Stearic acid | 2.0% |
| Polyoxyethylene (25) cetyl ether | 3.0% |
| Glyceryl monostearate | 2.0% |
| Octyldodecanol | 10.0% |

-continued

| | |
|---|---|
| Cetanol | 6.0% |
| Reduced lanolin | 4.0% |
| Squalane | 9.0% |
| 1,3-Butylene glycol | 6.0% |
| Polyethylene glycol (1500) | 4.0% |
| Preservative | appropriate amount |
| Perfume | appropriate amount |
| Distilled water | balance |

Blend Example 7 Cream

| | |
|---|---|
| N,N'-Bis(2-hydroxybenzyl)-L-cystine | 1.0% |
| Solid paraffin | 5.0% |
| Bee wax | 10.0% |
| Vaseline | 15.0% |
| Fluid paraffin | 41.0% |
| 1,3-Butylene glycol | 4.0% |
| Monostearate glycerin | 2.0% |
| Monolaurate polyoxyethylene sorbitan (20) | 2.0% |
| Borax | 0.2% |
| Preservative | appropriate amount |
| Perfume | appropriate amount |
| Anti-oxidant | appropriate amount |
| Distilled water | balance |

Blend Example 8 Emulsion

| | |
|---|---|
| N,N'-Bis(2-hydroxybenzyl)-L-cystine | 2.0% |
| Retinol | 0.1% |
| Bee wax | 0.5% |
| Vaseline | 2.0% |
| Monostearate glyceryl | 1.0% |
| Monooleate polyethylene glycol | 1.0% |
| Methylpolysiloxane | 2.0% |
| Cetanol | 1.0% |
| Squalane | 6.0% |
| Carboxyvinyl polymer | 0.5% |
| 1,3-Butylene glycol | 4.0% |
| Ethanol | 5.0% |
| Preservative | appropriate amount |
| Perfume | appropriate amount |
| Distilled water | balance |

Blend Example 9 Emulsion

| | |
|---|---|
| N,N'-Bis(2-hydroxybenzyl)-L-cystine | 1.0% |
| Stearyl alcohol | 0.5% |
| Hardened palm oil | 3.0% |
| Fluid paraffin | 35.0% |
| Dipropylene glycol | 6.0% |
| Polyethylene glycol (400) | 4.0% |
| Sesqui-oleate sorbitan | 1.6% |
| Polyoxyethylene (20) oleyl ether | 2.4% |
| Carboxyvinyl polymer | 1.5% |
| Potassium hydroxide | 0.1% |
| Chelator | appropriate amount |
| Preservative | appropriate amount |
| Perfume | appropriate amount |
| Distilled water | balance |

Blend Example 10 Gel

| | |
|---|---|
| N,N'-Bis(2-hydroxybenzyl)-L-cystine | 0.05% |
| Fluid paraffin | 12.0% |
| Tri(2-ethylhexanate) glyceryl | 50.0% |
| Sorbit | 10.0% |
| Polyethylene glycol (400) | 5.0% |
| Acylmethyl taurine | 5.0% |
| Polyoxyethylene (20) isocetyl ether | 10.0% |
| Perfume | appropriate amount |
| Preservative | appropriate amount |
| Distilled water | balance |

Blend Example 11 Aesthetic lotion

| | |
|---|---|
| N,N'-Bis(2-hydroxybenzyl)-L-cystine | 0.5% |
| Dipropylene glycol | 5.0% |
| Polyethylene glycol (400) | 5.0% |
| Ethanol | 10.0% |
| Carboxyvinyl polymer | 0.5% |
| Sodium alginate | 0.5% |
| Potassium hydroxide | 0.2% |
| Monostearate polyoxyethylene (20) | 1.0% |

-continued

| | |
|---|---|
| sorbitan | |
| Monooleate sorbit | 0.5% |
| Oleyl alcohol | 0.5% |
| Placenta extracts | 0.2% |
| Acetate dl-α-tocopherol | 0.2% |
| Perfume | appropriate amount |
| Preservative | appropriate amount |
| Browning-preventing agent | appropriate amount |
| Distilled water | balance |

Blend Example 12 Pack

| | |
|---|---|
| N,N'-Bis(2-hydroxybenzyl)-L-cystine | 3.0% |
| Polyvinyl alcohol | 15.0% |
| Carboxymethyl cellulose | 5.0% |
| 1,3-Butylene glycol | 5.0% |
| Ethanol | 12.0% |
| Polyoxyethylene (20) oleyl ether | 0.5% |
| Perfume | appropriate amount |
| Preservative | appropriate amount |
| Buffer | appropriate amount |
| Distilled water | balance |

Blend Example 13 Foundation

| | |
|---|---|
| N,N'-Bis(2-hydroxybenzyl)-L-cystine | 5.0% |
| Fluid paraffin | 10.0% |
| Monooleate polyoxyethylene (20) sorbitan | 3.5% |
| Propylene glycol | 3.0% |
| Titanium oxide | 9.0% |
| Kaolin | 24.0% |
| Talc | 42.0% |
| Coloring pigment | 3.0% |
| Perfume | appropriate amount |
| Preservative | appropriate amount |
| Anti-oxidant | appropriate amount |

Blend Example 14 Cleansing

| | |
|---|---|
| N,N'-Bis(2-hydroxybenzyl)-L-cystine | 0.5% |
| N-Lauroyl glutamate triethanolamine salt | 25.0% |
| Laurate triethanolamine | 5.0% |
| Polyoxyethylene (4) polyoxypropylene (11) butyl ether | 5.0% |
| Ethanol | 3.0% |
| Perfume | appropriate amount |
| Preservative | appropriate amount |
| Distilled water | balance |

Blend Example 15 Shampoo

| | |
|---|---|
| N,N'-Bis(2-hydroxybenzyl)-L-cystine | 0.5% |
| Polyoxyethylene (3) lauryl ether triethanolamine sulfate | 3.0% |
| Polyoxyethylene (3) lauryl ether sodium sulfate | 6.0% |
| Sodium laurylsulfate | 1.5% |
| Laurate diethanolamide | 3.0% |
| Lauryldimethylaminoacetate betaine | 2.5% |
| Cationated cellulose | 0.2% |
| Distearate ethylene glycol | 2.0% |
| Perfume | appropriate amount |
| Preservative | appropriate amount |
| Chelator | appropriate amount |
| Buffer | appropriate amount |
| Distilled water | balance |

Blend Example 16 Bathing agent (granule)

| | |
|---|---|
| N,N'-Bis(2-hydroxybenzyl)-L-cystine | 3.0% |
| Sodium sulfate | 44.0% |
| Sodium hydrogen carbonate | 45.0% |
| Borax | 2.0% |
| Carboxymethyl cellulose, sodium salt | 1.0% |
| Pigment | appropriate amount |
| Perfume | appropriate amount |

Numerous modifications and variations on the present invention are possible in light of the above teachings. It is, therefore, to be understood that within the scope of the accompanying claims, the invention may be practiced otherwise than as specifically described herein.

Advantages of the Present Invention

In accordance with the invention, an agent for suppressing activation of inflammatory factors can be provided. The agent of the present invention has a great inflammatory factor activation suppression activity. The agent for suppressing the activation of inflammatory factors is particularly prepared into a form suitable for pharmaceutical agents (such as, pharmaceutical products; external skin application agents, eye drops, nutrition agents, transfusion, and the like), cosmetics (including additives for cosmetics) or foods or drinks (health foods or drinks and the like) containing the specific cystine derivative as an effective ingredient. If necessary, further, appropriate carriers and additives may be blended in combination for use.

Particularly when coated on skin, the agent for suppressing activation of inflammatory factors is hardly dissociated from the skin but remains effectively on the skin with excellent touch during use. Therefore, the agent for suppressing activation of inflammatory factors is particularly preferred for cosmetics or a wide range of pharmaceutical products such as external skin application agents, for which such action and effect are desirably demanded.

Furthermore, the present invention provides a novel cystine derivative preferable as the effective ingredient (active ingredient) of an agent for suppressing activation of inflammatory factors, which has such great action for suppressing activation of inflammatory factors, a method for producing the same, and a method for suppressing the activation of inflammatory factors. The method for suppressing activation of inflammatory factors includes allowing a biological organism (living organism) to ingest or be given by the cystine derivative. Thereby the present invention provides a method for therapeutically treating, ameliorating and/or preventing diseases (disorders) involved in the activation of inflammatory factors, and a method for preventing, delaying, ameliorating and/or therapeutically treating skin change via aging or aesthetically unfavorable skin change as induced or promoted by inflammatory factors, and the like. Moreover, the present invention provides a use of the cystine derivative (active ingredient) as an agent for suppressing the activation of inflammatory factors.

Thus, the invention is very useful industrially in a great number of fields, particularly medical practices, pharmaceutical products (medicines), foods, cosmetics and the like.

What is claimed is:

1. A cystine derivative represented by formula (I):

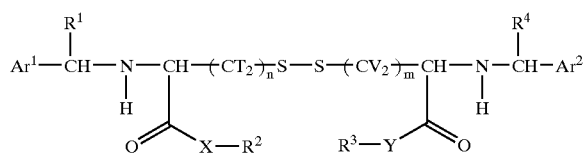

(I)

wherein

"n" and "m" independently represent an integer of 0 to 5;
$Ar^1$ and $Ar^2$ independently represent a 2-hydroxyaryl group wherein the 2-hydroxyaryl group may be independently substituted with at least one substituent selected from the group consisting of: halogen atom, hydroxyl group, cyano group, nitro group, amino group, $C_1$–$C_{20}$ alkyl group, $C_1$–$C_4$ alkyl group wherein at least a part of the hydrogen atoms is substituted with fluorine atom(s), $C_1$–$C_6$ alkoxy group, $C_1$–$C_6$ hydroxyalkyl group, and $C_1$–$C_6$ aminoalkyl group;

$R^1$ and $R^4$ independently represent a substituent selected from the group consisting of hydrogen atom, $C_1$–$C_6$ alkyl group, and phenyl group;

X and Y independently represent O;

$R^2$ and $R^3$ independently represent a substituent selected from the group consisting of hydrogen atom, $C_1$–$C_{20}$ alkyl group, $C_7$–$C_{16}$ aralkyl group, and $C_2$–$C_{20}$ unsaturated hydrocarbon group having unsaturated carbon-carbon bond(s) within the molecule; and the two Ts independently represent hydrogen atom or $C_1$–$C_6$ alkyl group and the two Vs independently represent hydrogen atom or $C_1$–$C_6$ alkyl group, and wherein the cystine derivative may be in a form selected from the group consisting of a free form, a salt form and a solvate form; and additionally wherein the cystine derivative may be an optically active substance or a racemic modification.

2. The cystine derivative according to claim 1, wherein the salt is selected from the group consisting of hydrochloride salt, sulfate salt, phosphate salt, nitrate salt, sodium salt, potassium salt, zinc salt and copper salt; and the solvate is a hydrate.

3. The cystine derivative according to claim 1, wherein $Ar^1$ and $Ar^2$ are 2-hydroxyphenyl group.

4. The cystine derivative according to claim 3, wherein X and Y are O.

5. The cystine derivative according to claim 1, wherein each "n" and "m" independently represent 1 or 2; the two Ts and the two Vs independently represent hydrogen atom or methyl group; $R^1$ and $R^4$ represent hydrogen atom; each X and Y independently represent O or NH; $R^2$ and $R^3$ independently represent hydrogen atom or $C_1$–$C_8$ alkyl group; $Ar^1$ and $Ar^2$ independently are selected from 2-hydroxyphenyl group, 2-hydroxypyridyl group and pyridyl group, which independently are unsubstituted or are substituted with one or more groups selected from the group consisting of hydroxyl group, $C_1$–$C_4$ alkyl group, $C_1$–$C_4$ alkoxy group, and $C_1$–$C_3$ hydroxyalkyl group.

6. The cystine derivative according to claim 1, which is N,N'-bis(2-hydroxybenzyl)-L-cystine.

7. The cystine derivative according to claim 6, wherein the N,N'-bis(2-hydroxybenzyl)-L-cystine is in any form selected from the group consisting of a dimethyl ester, a diethyl ester, and a diisopropyl ester.

8. A composition for suppressing the activation of inflammatory factor(s), wherein the composition comprises the cystine derivative according to claim 1 as an effective ingredient.

9. The composition for suppressing the activation of inflammatory factor(s) according to claim 8, which is in a form selected from the group consisting of a free form, a salt form, and a solvate form, which are acceptable for pharmaceuticals or cosmetics.

10. The composition for suppressing the activation of inflammatory factor(s) according to claim 8, wherein the inflammatory factor is IL-1α and/or NF-κB.

11. The composition for suppressing the activation of inflammatory factor(s) according to claim 8, which is in a form suitable for a therapeutic composition for mammals suffering from or being sensitive to a disease involved in the activation of inflammatory factor(s).

12. The composition for suppressing the activation of inflammatory factor(s) according to claim 11, wherein the disease involved in the activation of inflammatory factor(s)

is at least one disease selected from the group consisting of acute pain, chronic pain, shock via blood volume decrease, injuries shocks, blood reperfusion disorders, circulative shock, septic shock, systemic inflammation, systemic inflammation syndrome, local inflammation, pneumonia, bronchitis, pancreatitis, cerebral meningitis, encephalitis, ulcerative colitis, inflammatory bowel diseases, dermatitis, nephritis, arthritis, angitis, endocarditis, pleurisy, peritonitis, conjunctivitis, choroiditis, hyperparathyroidism, acne, psilosis, multiple sclerosis, transplant or graft rejection, autoimmune diseases, adult respiratory distress syndrome, osteoarthritis, rheumatoid arthritis, diabetes mellitus, diabetic neuropathy, diabetic renal disorders, diabetic cataract, atopic dermatitis, ileitis, ulcerative colitis, Crohn's disease, asthma, psoriasis, periodontis, apical cyst, nephrosis, central nervous system-demyelinating disorders, glaucoma, cataract, macular degeneration, lupus erythematosus, acquired immunodeficiency syndrome-related dementia, acquired immune deficiency syndrome-related complication, Alzheimer's disease, Huntington's disease, Parkinson's disease, neurodegenerative disease, neuron toxicity, migraine, chemical dependence and narcotics, vomiting, epilepsy, anxiety, memory disorders, depression, hyper kinetic syndrome, emotion disorders, aprosexia, schizophrenia, morphine-induced tolerance and withdrawal symptom, head injuries, acute spine injuries, thrombosis, platelet coagulation, atherosclerosis, ischemic cardiac diseases, cardiomyopathy, renal failure, glumerulonephritis, anadrenalism, acute pancreatitis, hyperchloresteremia, arteriosclerosis, osteogenic disorder and osteoporosis, bone diseases involved in the increase of bone resorption, pre-eclampsia, eclampsia, uremia complication, chronic liver failure, stroke, cerebral ischemia, cerebral hemorrhage and cancer.

13. The composition for suppressing the activation of inflammatory factor(s) according to claim 11, where the inflammatory disease is induced by ultraviolet ray.

14. The composition for suppressing the activation of inflammatory factor(s) according to claim 8, which is in a form suitable for oral, parenteral or local dosing.

15. The composition for suppressing the activation of inflammatory factor(s) according to claim 8, which is in a form suitable for eye drops.

16. The composition for suppressing the activation of inflammatory factor(s) according to claim 8, which is in a form suitable for addition to cosmetics.

17. The composition for suppressing the activation of inflammatory factor(s) according to claim 8, which is in a form suitable for an cosmetic application composition or an external skin application composition and may contain one or more carriers for cosmetics application compositions or for external skin application compositions.

18. The composition for suppressing the activation of inflammatory factor(s) according to claim 8, which is in a form selected from the group consisting of a food, a drink, a nutrition agent, and a transfusion dosage.

19. The composition for suppressing the activation of inflammatory factor(s) according to claim 8, wherein the cystine derivative of formula (I) is N,N'-bis(2-hydroxybenzyl)-L-cystine.

20. The cystine derivative according to claim 19, wherein the N,N'-bis(2-hydroxybenzyl)-L-cystine is in any form selected from the group consisting of a dimethyl ester, a diethyl ester, and a diisopropyl ester.

* * * * *